United States Patent [19]
Koike

[11] Patent Number: 6,077,719
[45] Date of Patent: Jun. 20, 2000

[54] SEMICONDUCTOR DEVICE EVALUATION METHOD, METHOD OF CONTROLLING THE SEMICONDUCTOR DEVICE PRODUCTION PROCESSES AND RECORDING MEDIUM

[75] Inventor: Norio Koike, Kyoto, Japan

[73] Assignee: Matsushita Electronics Corporation, Osaka, Japan

[21] Appl. No.: 09/120,890

[22] Filed: Jul. 23, 1998

[30] Foreign Application Priority Data

Jul. 24, 1997 [JP] Japan .................................. 9-198446

[51] Int. Cl.[7] .......................... G01R 31/26; H01L 21/00
[52] U.S. Cl. .................................. 438/17; 438/14; 438/18
[58] Field of Search .................................. 438/17, 18, 14, 438/15

[56] References Cited

U.S. PATENT DOCUMENTS 5,449,638  9/1995  Hong et al. .
5,686,346  11/1997  Duane .
5,773,989  6/1998  Edelman et al. .

OTHER PUBLICATIONS

A. Berman, "Time–Zero Dielectric Reliability Test by a Ramp Method", IEEE/PROC. IRPS, pp. 204–209, 1981.

K. Yamabe, et al. "Time–Dependent Dielectric Breakdown of Thin Thermally Frown $SiO_2$ Films", IEEE Transactions on Electron Devices, vol. ED–32, No. 2, pp. 423–428, Feb. 1985.

Published by Engineering Department of Electronic Industries Association, "Procedure for the Wafer–Level Testing of Thin Dielectrics", JEDEC Standard No. 35, pp. 1–39, Jul. 1992.

*Primary Examiner*—Kevin M. Picardat
*Assistant Examiner*—D. Mark Collins
*Attorney, Agent, or Firm*—McDermott, Will & Emery

[57] ABSTRACT

An electric field changing in the form of a ramp waveform with the passage of time is applied to an oxide layer, and the electric current densities applied to the oxide layer at measuring points of time are measured. The electric current densities applied until the oxide layer is broken down, are integrated with respect to time, thus obtaining a total electric charge amount Qbd used up to the breakdown of the oxide layer. The total electric charge amount Qbd is divided by each of the electric current densities at the measuring points of time, thus obtaining each of the estimated values of oxide layer lifetime at the time when it is supposed that each of the electric current densities at the points of time was constantly applied. Using the field intensities and the lifetime estimated values at the common measuring points of time, there is determined a regression line in which the oxide layer lifetime estimated values are expressed in the form of a function of the field intensities. Based on the regression line, a field acceleration coefficient is determined and the oxide layer lifetime at an optional field intensity is estimated.

13 Claims, 10 Drawing Sheets

SEMICONDUCTOR DEVICE EVALUATION METHOD, METHOD OF CONTROLLING THE SEMICONDUCTOR DEVICE PRODUCTION PROCESSES AND RECORDING MEDIUM

BACKGROUND OF THE INVENTION

The present invention relates to a method of evaluating the reliability or the like of an insulating layer of a semiconductor device, a semiconductor-device-production-process control method using this evaluation method, and a recording medium for causing a computer to execute the evaluation procedure.

With the recent demand for higher density, higher integration and miniaturization of a semiconductor integrated circuit device, an insulating layer, particularly a $SiO_2$ layer (hereinafter referred to as oxide layer), tends to be reduced in thickness in each of the MOS transistors or MOS capacitors forming the device. On the other hand, since the semiconductor integrated circuit device is not lowered in power voltage so much, the field intensity applied to the oxide layer is increased as the oxide layer is reduced in thickness. Under such circumstances, the time dependent dielectric breakdown (TDDB) of an oxide layer is now regarded as an important issue on which the reliability relies. More specifically, when an electric field is applied to the oxide layer, for example when a voltage is applied across the gate electrode and the channel region of a MOS transistor, or across two electrodes of a MOS capacitor, the oxide layer is broken down at the point of time when a certain period of time has passed from the start of application of the electric field. As a result, the oxide layer looses the electric insulating properties, causing the gate and channel or the upper and lower electrodes sandwiching the oxide layer to be electrically short-circuited. The period of time above-mentioned will be hereinafter referred to as oxide layer lifetime.

Examples of the TDDB include (i) an intrinsic failure which occurs in an originally good oxide layer when a predetermined period of time has passed from the start of application of a voltage and in which the incidence distribution function has a peak, and (ii) an accidental failure which occurs in an originally defective oxide layer earlier than an intrinsic failure. Burn-in is executed for screening an accidental failure of oxide layer of each product. The burn-in condition is determined as follows. First, a field acceleration coefficient of the stress is obtained from the field-intensity-dependency of the oxide layer intrinsic failure periods (lifetimes) obtained through a TDDB test. With the use of the field acceleration coefficient, the burn-in condition is determined as a condition under which an oxide layer accidental failure can be screened within the range where no oxide layer intrinsic failure occurs. As the field acceleration coefficient of the stress for an accidental failure, there is used the field acceleration coefficient measured for the intrinsic failure.

Thus, a time dependent dielectric breakdown test (TDDB test) for extraction of a field acceleration coefficient and estimation of an oxide layer lifetime, is essential in designing and developing a semiconductor integrated circuit device, and tends to be increasingly important.

Examples of the time dependent dielectric breakdown test (TDDB test) include, as shown in the following Table, a constant voltage test in which constant voltages are applied until insulating layers are broken down, a constant electric current test in which constant electric currents are applied until insulating layers are broken down, a ramp voltage test in which a voltage increasing at a constant increasing rate with the passage of time, is applied to the insulating layer, and a ramp (electric current test in which an electric current increasing at a constant increasing rate with the passage of time, is applied to the insulating layer.

TABLE

| Test Type | Object | Test Time | Information to be Obtained |
|---|---|---|---|
| Constant voltage test | Estimation of actual-use lifetime (Absolute evaluation) | long | τ (lifetime) |
| Constant electric current test | Evaluation of oxide layer in quality (Relative evaluation) | long | Qbd (Breakdown electric charge amount) |
| Ramp voltage test | Evaluation of oxide layer in defect (Relative evaluation of accidental failure) | short | Ebd (Dielectric strength) |
| Ramp electric current test | Evaluation of oxide layer in quality (Relative evaluation) | short | Qbd (Breakdown electric charge amount) |

Of the tests above-mentioned, the constant voltage test is to be conducted to estimate an actual-use lifetime τ. By this test, an absolute evaluation can be made on the lifetime of the insulating layer. The constant electric current test is to be conducted to obtain an electric charge to breakdown Qbd serving as an index based on which the insulating layer is evaluated in quality. By this test, a relative evaluation can be made on the quality of the insulating layer. The ramp voltage test is to be conducted to obtain the breakdown electric field Ebd serving as an index based on which the insulating layer is evaluated in defect density. By this test, a relative evaluation can be made on the incidence of accidental failure. Likewise the constant electric current test, the ramp electric current test is to be conducted to obtain the electric charge to breakdown Qbd. By this test, a relative evaluation can be made on the quality of the insulating layer. It is noted that when finely checked for waveform, the voltage and electric current in actually conducted ramp voltage and electric current tests, mostly undergo a gradual change and hardly increase perfectly continuously with the passage of time.

With reference to FIG. 9 to FIG. 11, the following description will discuss a conventional constant voltage test for extracting a field acceleration coefficient and estimating an oxide layer lifetime. FIG. 9 is a flow chart illustrating the steps of estimating an oxide layer lifetime through a conventional constant voltage TDDB test. FIG. 10 is a view illustrating the results of measurement of oxide layer lifetime at each stress field intensity, obtained through the conventional constant voltage TDDB test. FIG. 11 is a view illustrating a method of finally determining the oxide layer lifetime in the conventional constant voltage TDDB test.

As shown in FIG. 9, at a step ST51, constant voltages are applied to oxide layers through two conductive layers which sandwich the oxide layers. At a step ST52, there are measured the periods of time (oxide layer lifetimes) between the starts of voltage application and the breakdown of the oxide layers. At a step ST53, the oxide layer lifetimes at the respective field intensities are approximated in the form a function of the field intensities. At a step ST54, a field acceleration coefficient is extracted from the function and the oxide layer lifetime at an optional field intensity is estimated. According to these steps, the stress oxide layer lifetime is estimated.

FIG. 10 is a view illustrating in detail the steps ST51 and ST52. In FIG. 10, the axis of abscissa represents stress time at which an electric field is applied to oxide layers, the right-hand axis of ordinate represents the accumulated failure rate P due to time dependent dielectric breakdown of oxide layers, and the left-hand axis of ordinate represents $\ln\{-\ln(1-p)\}$ calculated from the accumulated failure rate P. Black triangle points, white circle points, white square points and white triangle points respectively represent the accumulated failure rates at the points of time when oxide layers were broken at the stress field intensities Ea, Eb, Ec, Ed. Straight lines ap, bp, cp, dp connecting points of the same types, represent the time dependencies of accumulated failure rates at the respective stress field intensities Ea, Eb, Ec, Ed. Respective stress times Ta, Tb, Tc, Td at the intersecting points where the respective straight lines intersect the long and short dash line, are the measured values of 50% accumulated failure time due to time dependent dielectric breakdown of oxide layers. As shown in FIG. 10, plotting the accumulated failure rates P on a graph having a logarithm of time on the axis of abscissa and $\ln\{-\ln(1-p)\}$ on the axis of ordinate, is generally called a Weibull plotting. Generally, when the failure probability follows a Weibull distribution, the results of Weibull plotting are represented in the form of a straight line. When it is desired to express, on a graph, the accumulated failure rates of time dependent dielectric breakdown of oxide layers with respect to stress times, a Weibull plotting method is widely used.

FIG. 11 is views illustrating in detail the steps ST53 and ST54. In FIG. 11, the axis of abscissa represents the field intensity E applied to oxide layers and the axis of ordinate represents the oxide layer lifetime T. In FIG. 11, Ta, Tb, Tc, Td refer to the measured values of 50% accumulated failure time, EA, EB, EC, ED refer to stress field intensities, a straight line T(E) represents an estimation line of oxide layer lifetime, Emax is the maximum field intensity applied to the oxide layer when the oxide layer is actually used, and τES is an estimated value of oxide layer lifetime when the oxide layer is actually used.

The following description will discuss a specific process for executing the steps above-mentioned. To estimate an oxide layer lifetime, there are prepared a number of MOS capacitors respectively having, as capacitor insulating layers, oxide layers identical in shape, sizes and production process with one another. These MOS capacitors are divided into a plurality of groups. There is applied, to each of the groups, each of the constant stress field intensities EA, EB, EC, ED which are higher than the maximum field intensity Emax which is shown in FIG. 11 and which is to be applied to each oxide layer at a normal operating condition. By such stress application, oxide layers of each group experience a time dependent dielectric breakdown and the number of failed oxide layers is increased with the passage of time.

The periods of time (stress periods of time) between the starts of application of stress field intensities and the breakdowns of oxide layers, and the accumulated failure rates; at the points of time of such breakdowns, are plotted in a Weibull manner as shown in FIG. 10. Empirically, the failure rates of time dependent dielectric breakdown of oxide layers follow a Weibull distribution. Accordingly, each Weibull plotting of time-dependent accumulated failure rates is generally expressed in the form of a straight line. Based on these data, there are obtained regression lines ap, bp, cp, dp for the accumulated failure rates at the points of time when oxide layers are broken down at stress field intensities, and there are obtained the actually measured values Ta, Tb, Tc, Td of 50% accumulated failure time, i.e., the periods of time during which the accumulated failure rates reach 50% at the respective stress field intensities EA, EB, EC, ED.

With the 50% accumulated failure times regarded as oxide layer lifetimes, there are plotted, in a semi-logarithmic graph in FIG. 11, the actually measured values Ta, Tb, Tc, Td of 50% accumulated failure time on the axis of ordinate, and the field intensities EA, EB, EC, ED applied to the oxide layers on the axis; of abscissa. Empirically, the actually measured values Ta, Tb, Tc, Td of 50% accumulated failure time can be plotted on a straight line. Based on this, the actually measured values Ta, Tb, Tc, Td, of 50% accumulated failure time, i.e., the oxide layer lifetimes T, are approximated in the form of a function of field intensity E, e.g., in the form of a regression line T(E). The slope of the regression line T(E) is extracted as a stress field acceleration coefficient β (decades/MV/cm). Using this regression line T(E), there can be obtained the estimated value of oxide layer lifetime at an optional field intensity. Then, there is obtained the lifetime estimated value τES of oxide layer at a normal operating condition, i.e., at the maximum value Emax of field intensity actually applied to the oxide layer.

To evaluate, in a short period of time, the reliability of oxide layers with the use of MOS capacitors on a wafer for which the diffusion step has been finished in a production process, a test is to be conducted, on a wafer level, on a plurality of MOS capacitors each having, as a capacitor insulating layer, an oxide layer to be evaluated. Using an automatic prober, the test is to be conducted on the MCS capacitors on a wafer with the measurement points successively probed.

Of the conventional methods of estimating the oxide layer lifetime, the constant voltage test has the following problems.

In development of a semiconductor device production process, a process condition is frequently changed. A change in process condition likely changes the field acceleration coefficient and the oxide layer lifetime. It is therefore required to frequently conduct an extraction of field acceleration coefficient and an estimation of oxide layer lifetime.

In a mass production at a factory, there are instances where a process condition is changed due to trouble of a production machine or the like such that the wafers for which the diffusion step has been finished, vary in oxide layer lifetime. In the worst case, there is produced a wafer having an oxide layer of which lifetime is too short to satisfy the standards for assuring the reliability. If such an abnormality occurs, to prevent a product low in reliability from being delivered from the factory to the market, it is required to rapidly and accurately estimate the lifetimes of the oxide layers.

More specifically, it is required to obtain, in a short period of time, the field acceleration coefficient and the estimated oxide layer lifetime for each of the wafers for which the diffusion step has been finished.

When conducting a test of lifetime estimation on a wafer level according to any of the conventional oxide layer lifetime estimating methods above-mentioned, an automatic prober is used for measurement in which the MOS capacitors on a wafer are successively probed. Accordingly, the number of MOS capacitors which can simultaneously be subjected to the test, is limited to one or several which can simultaneously be electrically connected to the probe needles of a probe card. Thus, when a number of stress field intensities are applied to a number of MOS capacitors to measure the accumulated failure rates, this takes much time. In particular, this is remarkable in measurement at low stress field intensities and therefore constitutes a great hindrance to the extraction of field acceleration coefficients and estimation of oxide layer lifetimes of all the wafers.

To shorten the period of time for estimation of oxide layer lifetime, the number of MOS capacitors to be used can be reduced or the stress field intensities to be used in the test can be increased.

However, it is required to obtain the accumulated failure rates using a variety of different stress field intensities. Accordingly, when the number of MOS capacitors to be used in the measurement is reduced, the number of MOS capacitors assigned for each stress field intensity condition is further reduced. Even though it is supposed that the MOS capacitors on a single wafer are equivalent to one another, the MOS capacitors are actually different in characteristics from one another. The accumulated failure rate at each stress field intensity is obtained from different MOS capacitors. Therefore, as the number of MOS capacitors assigned to each stress field intensity is smaller, the variations in characteristics of the MOS capacitors appear in the form of displacement of the distribution of accumulated failure rate at each stress field intensity. As a result, the variations in characteristics of the MOS capacitors appear in the form of displacement of oxide layer lifetime at each stress field intensity. This finally increases the errors in the field acceleration coefficient and the estimated value of oxide layer lifetime. In view of assurance of reliability, it is therefore not recommended to estimate the field acceleration coefficients and oxide layer lifetimes of all the wafers with MOS capacitors to be used for measurement being reduced in number in order to shorten the whole measuring period of time.

On the other hand, when the stress field intensities are increased, the following problems are encountered. First, the measuring device becomes poor in time precision. Further, the application of high electric fields generates a large amount of heat, causing the oxide layers to be unforeseeably increased in temperature. This shortens the periods of time between the starts of application of electric fields and the time-dependent dielectric breakdowns of the oxide layers, as compared with the periods of time taken with the use of the normal temperatures and field intensities. This produces great errors in the extraction of field acceleration coefficient and lifetime estimation. It is therefore not recommended to extract the field acceleration coefficients and to estimate the oxide layer lifetimes of all the wafers with the stress field intensities increased in order to shorten the whole measuring period of time.

Now, studies are also made for other TDDB tests than the constant voltage test. The constant electric current test can be shorter in test period of time than the constant voltage test, but still takes much time and is disadvantageous in that only relative evaluation of oxide layer in quality can be made. The ramp voltage test is shorter in test period of time, but is not fit for the object of evaluating the normal insulating layer lifetime. That is, there is obtained, by this test, information for estimating the incidence of accidental failure due to defect. The ramp electric current test is short in test period of time, but is also disadvantageous likewise the constant electric current test.

After all, according to any of the conventional test methods above-mentioned, there cannot be obtained, in a practically short period of time, a field acceleration coefficient and an oxide layer lifetime estimated value which are practically highly precise. In particular, it is not possible to extract the field acceleration coefficients of all the wafers and to estimate the oxide layer lifetimes of all the wafers.

SUMMARY OF THE INVENTION

It is an object of the present invention to provide a semiconductor device evaluation method (i) by which an evaluation result can be obtained in a practically short period of time with high precision, (ii) which comprises the step of extracting a field acceleration coefficient or estimating an insulating layer lifetime, the extracted field acceleration coefficient and the estimated lifetime value being compatible with those obtained according to a conventional method, thus making it possible to measure, in a short period of time, the field acceleration coefficients and insulating layer lifetime estimated values of all wafers under production, and (iii) which can monitor, without fail, changes in field acceleration coefficient and insulating layer lifetime due to changes in process conditions at the time of development of production process, or changes in field acceleration coefficient and insulating layer lifetime due to changes in process conditions due to trouble of a production machine or the like at the time of mass production of semiconductor devices at factory.

It is another object of the present invention to provide a semiconductor device production process control method with the use of the estimation method above-mentioned, and also to provide a recording medium arranged to cause a computer to execute the evaluation step.

A first semiconductor device evaluation method according to the present invention comprises: a first step of applying, to an insulating layer disposed in a semiconductor device, an electric field of which intensity undergoes a change with the passage of time; a second step of measuring the electric current densities applied to the insulating layer at a plurality of points of time during the application of the electric field; a third step of integrating, with respect to time, the electric current densities applied until the insulating layer is broken down, thereby to calculate the amount of electric charge used until the insulating layer is broken down; a fourth step of dividing the insulating layer electric charge to breakdown calculated at the third step, by each of the electric current densities at the points of time measured at the second step, thereby to obtain each of the estimated values of insulating layer lifetime at the time when it is supposed that each of the electric current densities at the points of time was constantly applied; a fifth step of approximating the insulating layer lifetime estimated values in the form of a function of the field intensities; and a sixth step of conducting, based on the function, at least one of an extraction of field acceleration coefficient and an estimation of the insulating layer lifetime at an optional field intensity.

According to the method above-mentioned, the electric current density applied to the insulating layer changes, with the passage of time, according to changes of the applied voltage with the passage of time. Based on the empirical fact that the total amount of electric charge used up to the breakdown of the insulating layer is a fixed value independent from the field intensity and the electric current density, there are obtained insulating layer lifetime estimated values at the time when it is supposed that the electric current densities at points on a time-dependent change characteristic line of the electric current density, were constantly applied to the insulating layer. Further, based on the lifetime estimated values thus obtained, there is determined a function of the lifetime estimated values with respect to the electric field. More specifically, unlike the conventional lifetime estimation method in which a plurality of constant voltages are applies to a plurality of points of MOS capacitors, the present invention is arranged such that a time-varying voltage is applied to a single point, thus producing effects identical with those produced by conducting a test with a plurality of constant voltages applied to a plurality of points. Thus, according to the present invention, the measuring period of time can be reduced in a practically short range, yet assuring the necessary measurement precision.

In the first semiconductor device evaluation method above-mentioned, at the sixth step, at least the extraction of field acceleration coefficient may be conducted, and using the field acceleration coefficient thus extracted, there may be determined the burn-in condition for a product in which the insulating layer is used.

As mentioned earlier, insulating layer lifetime estimated value are obtained based on the widely known empirical fact that the total amount of electric charge used up to the breakdown of the insulating layer is a fixed value independent from the field intensity and the electric current density. Accordingly, the obtained field acceleration coefficient and insulating layer lifetime estimated values at respective electric current densities, are highly compatible with those obtained according to the conventional method. Therefore, utilizing the fact that the field acceleration coefficient obtained at the sixth step, is highly compatible with that obtained according to the conventional method, it is possible to properly determine, in a short period of time, the burn-in condition with the use of the field acceleration coefficient above-mentioned.

In the first semiconductor device evaluation method above-mentioned, there is preferably used, at the first step, an electric field of which intensity between measuring points of time is incremental.

According to the method above-mentioned, even though the total amount of electric charge applied to the insulating layer until the insulating layer is broken down, is extremely small, the electric current density at an early stage of stress application can sufficiently be reduced. It is therefore possible to lengthen the period of time between the stress application and the breakdown of the insulating layer, to the extent that the necessary measurement precision can be assured. On the contrary, even though the total electric charge amount is extremely large, the electric current density immediately before the breakdown can sufficiently be increased. This prevents the measuring period of time from being lengthened. It is therefore possible to obtain an insulating layer lifetime estimated value in such a short period of time that this method can be executed in a production process.

Further, since there is used an electric field of which intensity is increased with the passage of time, it is possible to obtain, through measurement of electric current, voltage and the like of a MOS capacitor, an insulating layer lifetime estimated value of the MOS capacitor itself at a normal operating condition. Thus, according to the present invention, there is not increased the error in a field acceleration coefficient or insulating layer lifetime estimated value, unlike in the conventional insulating layer lifetime estimation method using different MOS capacitors. That is, in spite of reduction in measuring period of time, the estimation precision can be maintained at a level not less than that obtained by the conventional estimation method.

In the first semiconductor device evaluation method, there may be used, at the first step, an electric field constant in the rate of increase in intensity between measuring points of time.

In the first semiconductor device evaluation method, there may be used, at the first step, an electric field of which intensity changes in stages with the passage of time.

According to each of the methods above-mentioned, there may be used a device having no function for generating a voltage which is continuously increased.

In the first semiconductor device evaluation method, the first to sixth steps may be executed, simultaneously with measurement of breakdown electric filed, on each of the same samples used in this measurement.

In the first semiconductor device evaluation method, the evaluation test may be conducted, simultaneously with a ramp voltage TDDB test, on each of the same samples used in this TDDB test.

According to each of the methods above-mentioned, there is no need to prepare a dedicated sample for the evaluation test. Thus, a reliability evaluation of insulating layer on a wafer level can be made simultaneously with another reliability evaluation. Accordingly, more information relating to the reliability can be obtained to remarkably enhance the precision of reliability evaluation on insulating layer.

A second semiconductor device evaluation method according to the present invention comprises: a first step of applying, to an insulating layer disposed in a semiconductor device, an electric current of which density undergoes a change with the passage of time; a second step of measuring the electric field intensities applied to the insulating layer at a plurality of points of time during the application of the electric current; a third step of integrating, with respect to time, the electric current densities applied until the insulating layer is broken down, thereby to calculate the amount of electric charge used until the insulating layer is broken down; a fourth step of dividing the insulating layer electric charge to breakdown calculated at the third step, by each of the electric current densities at the points of time measured at the second step, thereby to obtain each of the estimated values of insulating layer lifetime at the time when it is supposed that each of the electric current densities at the points of time was constantly applied; a fifth step of approximating the insulating layer lifetime estimated values in the form of a function of the field intensities; and a sixth step of conducting, based on the function, at least one of an extraction of field acceleration coefficient and an estimation of the insulating layer lifetime at an optional field intensity.

According to the method above-mentioned, based on the empirical fact that the total amount of electric charge used up to the breakdown of the insulating layer is a fixed value independent from the field intensity and the electric current density, there is obtained each of insulating layer lifetime estimated values at the time when it is supposed that each of the electric current densities at points on the time-dependent change characteristic line of electric current density, was constantly applied to the insulating layer. Further, based on these lifetime estimated values, there is determined a function of the lifetime estimated values with respect to the electric field. More specifically, unlike the conventional lifetime estimation method in which a plurality of constant electric fields are applied to a plurality of points of MOS capacitors, the present invention is arranged such that a time-varying electric current density is applied to a single point, thus producing effects identical with those produced by conducting a test with a plurality of constant electric currents applied to a plurality of points. Thus, according to the present invention, the measuring period of time can be reduced in a practically short range, yet assuring the necessary measurement precision.

In the second semiconductor device evaluation method, at the sixth step, at least the extraction of field acceleration coefficient may be conducted, and using the field acceleration coefficient thus extracted, there may be determined the burn-in condition for a product in which the insulating layer is used.

As mentioned earlier, insulating layer lifetime estimated values are obtained based on the widely known empirical fact that the total amount of electric charge used up to the breakdown of the insulating layer is a fixed value independent from the field intensity and the electric current density. Accordingly, the obtained field acceleration coefficient and insulating layer lifetime estimated values at electric current densities, are highly compatible with those obtained according to the conventional method. Therefore, utilizing the fact that the field acceleration coefficient obtained at the sixth step, is highly compatible with that obtained according to the conventional method, it is possible to properly determine, in a short period of time, the burn-in condition with the use of the field acceleration coefficient above-mentioned.

In the second semiconductor device evaluation method, there is preferably used, at the first step, an electric current of which density between measuring points of time is incremental.

According to the method above-mentioned, there is used an electric current density which is increased with the passage of time. Therefore, even though the total amount of electric charge applied to the insulating layer until the insulating layer is broken down, is extremely small, the electric current density at an early stage of stress application can sufficiently be reduced. It is therefore possible to lengthen the period of time between the stress application and the breakdown of the insulating layer, to the extent that the necessary measurement precision can be assured. On the contrary, even though the total electric charge amount is extremely large, the electric current density immediately before the breakdown can sufficiently be increased. This prevents the measuring period of time from being lengthened. It is therefore possible to obtain an insulating layer lifetime estimated value in such a short period of time that this method can be executed in a production process.

Further, since there is used an electric current density which is increased with the passage of time, it is possible to obtain, through measurement of electric current and voltage of a MOS capacitor, an insulating layer lifetime estimated value of the MOS capacitor itself at a normal operating condition. Thus, according to the present invention, there is not increased the error in a field acceleration coefficient or insulating layer lifetime estimated value, unlike in the conventional insulating layer lifetime estimation method using different MOS capacitors. That is, even though the measuring period of time is reduced, the estimation precision of the second estimation method is not lowered but can be maintain at a level not less than that obtained by the conventional estimation method.

In the second semiconductor device evaluation method, there may be used, at the first step, an electric current constant in the logarithmic increase rate of electric current density between measuring points of time.

According to the method above-mentioned, it is possible to readily generate an electric current density which increases with the passage of time.

In the second semiconductor device evaluation method, there may be used, at the first step, an electric current of which density changes in stages with the passage of time.

According to the method above-mentioned, it is possible to use a device having no function for generating an electric current density which continuously changes.

In the second semiconductor device evaluation method, the reliability test may be conducted, simultaneously with a ramp electric current TDDB test, on each of the same samples used in this TDDB test.

According to the method above-mentioned, there is no need to prepare a dedicated sample for the reliability test. Thus, a reliability evaluation of insulating layer on a wafer level can be made simultaneously with another reliability evaluation. Accordingly, more information relating to the reliability can be obtained to remarkably enhance the precision of reliability evaluation on insulating layer.

A first semiconductor device production process control method according to the present invention comprises: a process for forming, on a semiconductor substrate, a first conductor layer, a second conductor layer and an insulating layer held by and between the first and second conductor layers; a process for estimating the lifetime of the insulating layer; and a process for controlling, based on the result of lifetime estimation of the insulating layer, the conditions under which such first and second conductor layers and insulating layer are produced. In this first method, the process for estimating the lifetime of the insulating layer comprises: a step of applying, to the insulating layer, an electric field of which intensity undergoes a change with the passage of time; a step of measuring the electric current densities applied to the insulating layer at a plurality of points of time during the application of the electric field; a step of integrating, with respect to time, the electric current densities applied until the insulating layer is broken down, thereby to calculate the amount of electric charge used until the insulating layer is broken down; a step of dividing the insulating layer electric charge to breakdown calculated at the third step, by each of the electric current densities at the points of time measured at the second step, thereby to obtain each of the estimated values of insulating layer lifetime at the time when it is supposed that each of the electric current densities at the points of time was constantly applied; a step of approximating the insulating layer lifetime estimated values in the form of a function of the field intensities; and a step of estimating, based on the function, the insulating layer lifetime at an optional field intensity.

In the first semiconductor device production process control method, the insulating layer lifetime estimation process is preferably executed on the semiconductor substrate which is in a wafer level.

A second semiconductor device production process control method comprises: a process for forming, on a semiconductor substrate, a first conductor layer, a second conductor layer and an insulating layer held by and between the first and second conductor layers; a process for estimating the lifetime of the insulating layer; and a process for controlling, based on the result of lifetime estimation of the insulating layer, the conditions under which such first and second conductor layers and insulating layer are produced. In this second method, the process for estimating the lifetime of the insulating layer comprises: a step of applying, to the insulating layer, an electric current of which density undergoes a change with the passage of time; a step of measuring the electric field intensities applied to the insulating layer at a plurality of points of time during the application of the electric current; a step of integrating, with respect to time, the electric current densities applied until the insulating layer is broken down, thereby to calculate the amount of electric charge used until the insulating layer is broken down; a step of dividing the insulating layer electric charge to breakdown calculated at the third step, by each of the electric current densities at the points of time measured at the second step, thereby to obtain each of the estimated values of insulating layer lifetime at the time when it is supposed that each of the electric current densities at the points of time was constantly applied; a step of approximating the insulating layer lifetime estimated values in the form of a function of the field intensities; and a step of estimating the lifetime of the insulating layer based on the function.

In the second semiconductor device production process control method, the insulating layer lifetime estimation process is preferably executed on the semiconductor substrate which is in a wafer level.

According to each of the first and second semiconductor device production process control methods, all wafers can be monitored, in a short period of time, for a change in insulating layer lifetime due to changes in process conditions due to trouble of a production machine or the like. This enables to produce highly reliable semiconductor devices with low costs.

A first recording medium according to the present invention, is arranged to be incorporated in and read by a computer to be used for evaluating the characteristics of a semiconductor device having an insulating layer, and contains a program to cause the computer to execute: a first step of applying, to the insulating layer of a semiconductor device, an electric field of which intensity undergoes a change with the passage of time; a second step of measuring the electric current densities applied to the insulating layer at a plurality of points of time during the application of the electric field; a third step of integrating, with respect to time, the electric current densities applied until the insulating layer is broken down, thereby to calculate the amount of electric charge used until the insulating layer is broken down; a fourth step of dividing the insulating layer electric charge to breakdown calculated at the third step, by each of the electric current densities at the points of time measured at the second step, thereby to obtain each of the estimated values of insulating layer lifetime at the time when it is supposed that each of the electric current densities at the points of time was constantly applied; a fifth step of approximating the insulating layer lifetime estimated values in the form of a function of the field intensities; and a sixth step of conducting, based on the function, at least one of an extraction of field acceleration coefficient and an estimation of the insulating layer lifetime at an optional field intensity.

A second recording medium according to the present invention is arranged to be incorporated in and read by a computer to be used for evaluating the characteristics of a semiconductor device having an insulating layer, and contains a program to cause the computer to execute: a first step of applying, to the insulating layer of a semiconductor device, an electric current of which density undergoes a change with the passage of time; a second step of measuring the electric field intensities applied to the insulating layer at a plurality of points of time during the application of the electric current; a third step of integrating, with respect to time, the electric current densities applied until the insulating layer is broken down, thereby to calculate the amount of electric charge used until the insulating layer is broken down; a fourth step of dividing the insulating layer electric charge to breakdown calculated at the third step, by each of the electric current densities at the points of time measured at the second step, thereby to obtain each of the estimated values of insulating layer lifetime at the time when it is supposed that each of the electric current densities at the points of time was constantly applied; a fifth step of approximating the insulating layer lifetime estimated values in the form of a function of the field intensities; and a sixth step of conducting, based on the function, at least one of an extraction of field acceleration coefficient and an estimation of the insulating layer lifetime at an optional field intensity.

A computer incorporating the first or second recording medium is utilized for estimating the lifetime of an insulat-

DETAILED DESCRIPTION OF PREFERRED EMBODIMENTS (First Embodiment)

Figure 1:
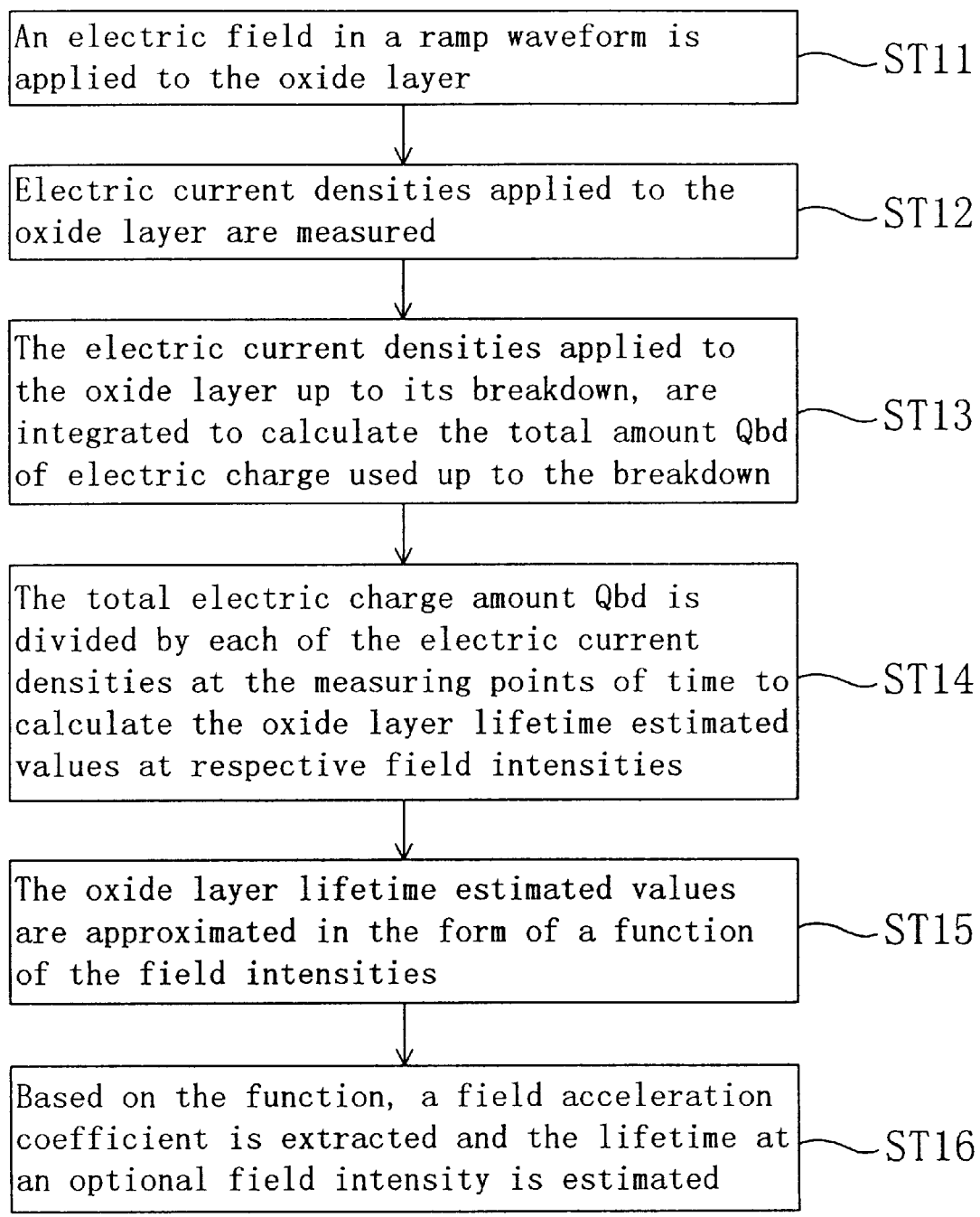
FIG. 1 is a flow chart illustrating the steps of a method of estimating an oxide layer lifetime through a ramp voltage TDDB test, according to a first embodiment of the present invention.
Figure 2:
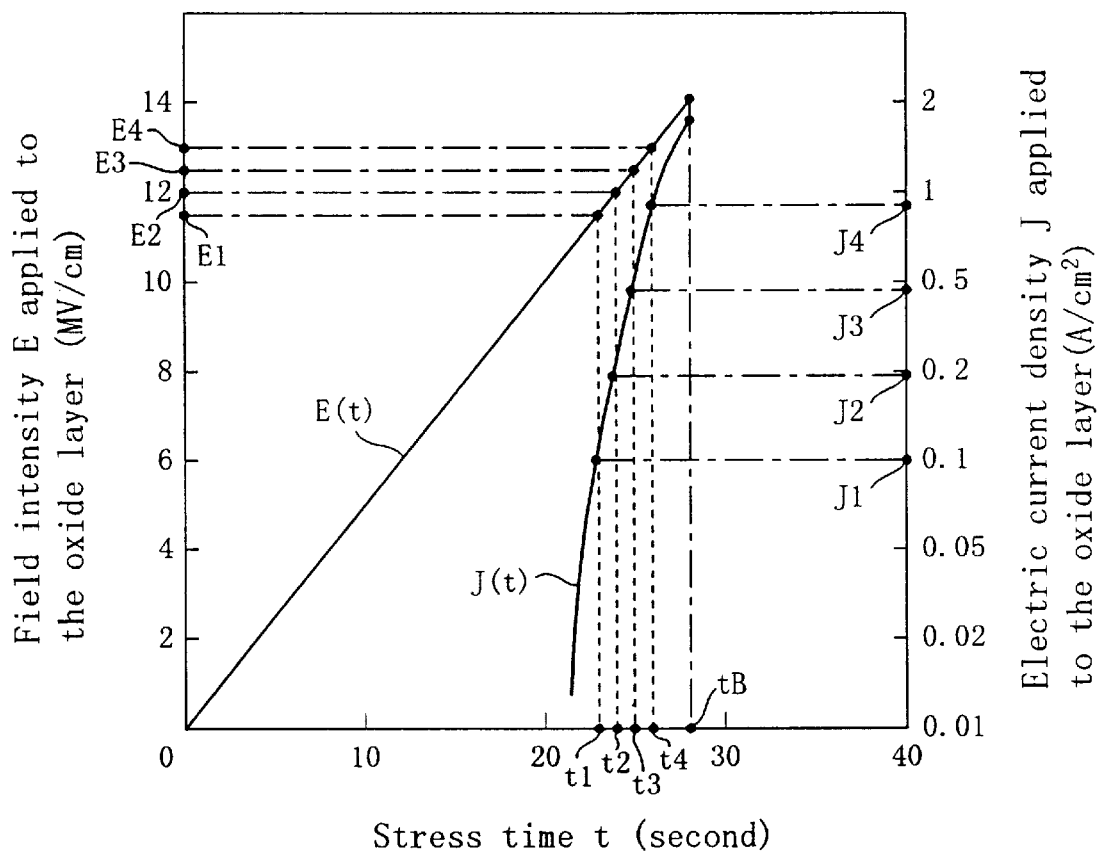
FIG. 2 is a view illustrating the waveform of the ramp voltage and the measurement results of electric current densities applied to the oxide layer at the time when the ramp field intensity is applied to the oxide layer, according to the first embodiment.
Figure 3:
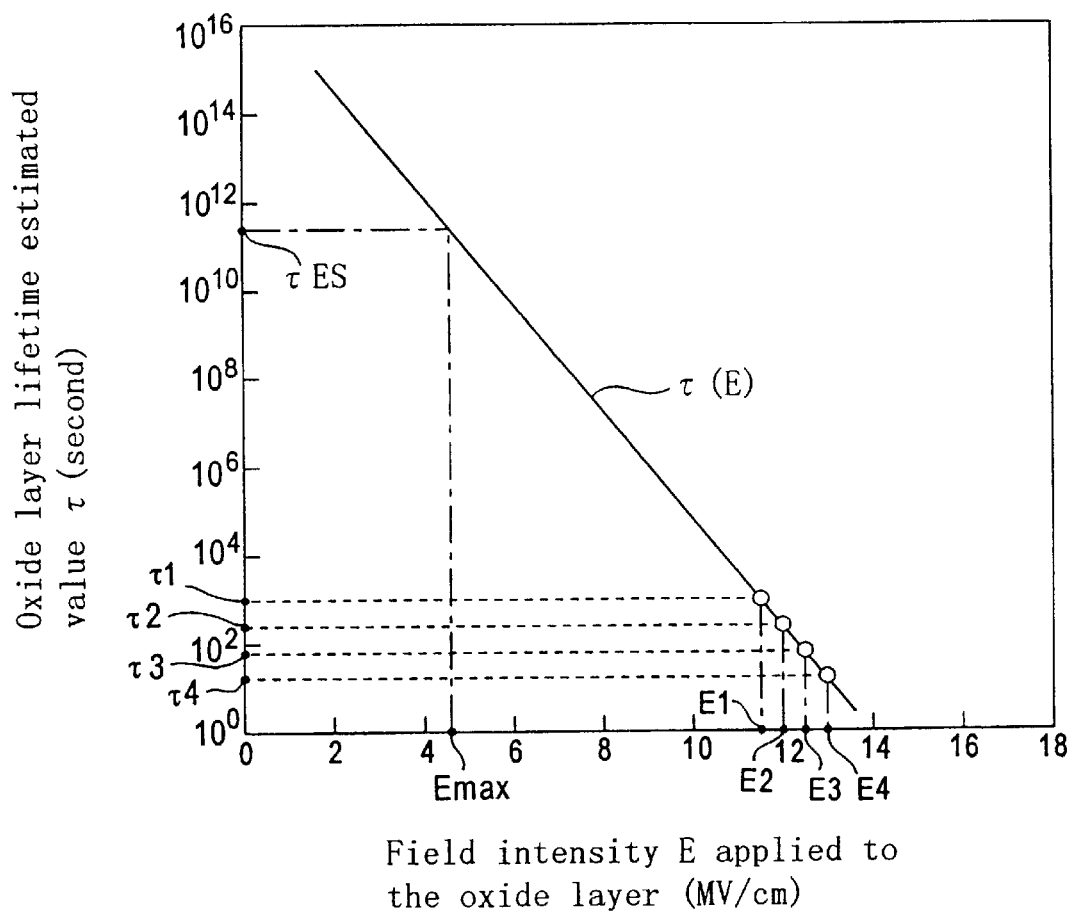
FIG. 3 is a view illustrating a regression line which represents, in the form of a function of the applied voltages, the oxide layer lifetime estimated values obtained according to the first embodiment, and also illustrating a method of extracting a field acceleration coefficient and estimating an oxide layer lifetime, these extraction and estimation being conducted with the use of this regression line.

The following description will discuss a first embodiment of the present invention with reference to FIG. 1 to FIG. 3. FIG. 1 is a flow chart illustrating the steps of conducting an oxide layer lifetime estimation through a TDDB test using a voltage having a ramp waveform (ramp voltage), according to the first embodiment. FIG. 2 is a view illustrating the measurement results of oxide layer lifetime at stress field intensities obtained through the ramp voltage TDDB test, and FIG. 3 is a view illustrating the steps of obtaining a regression line τ (E) through the ramp voltage TDDB test, and the steps of obtaining, using this regression line τ(E), the oxide layer lifetime at an optional applied voltage.

In FIG. 2, the axis of abscissa represents stress time t at which a voltage is applied to an oxide layer, the left-hand axis of ordinate represents the field intensity E applied to the oxide layer, and the right-hand axis of ordinate represents the current density J applied to the oxide layer. In FIG. 2, E(t) refers to the field intensity which is applied to the oxide layer and which changes in the form of a function of time t while describing a ramp waveform; E1, E2, E3, E4 refer to the field intensities which are respectively applied to the oxide layer at stress application times t1, t2, t3, t4 and which follow the ramp waveform of the field intensity E(t); J(t) refers to the electric current density which is applied to the oxide layer and which is expressed in the form of a function with respect to time t; J1, J2, J3, J4 refer to the electric current densities applied to the oxide layer at the field densities E1, E2, E3, E4; and tB refers to the stress application time at which the oxide layer is broken down.

In FIG. 3, the axis of abscissa represents the field intensity E applied to the oxide layer and the axis of ordinate represents the estimated value τ of oxide layer lifetime. In FIG. 3, τ1, τ2, τ3, τ4 refer to the estimated values of oxide layer lifetime at the field densities E1, E2, E3, E4 applied to the oxide layer; τ(E) refers to a lifetime estimation line (regression line) expressed in the form of a function of the applied field intensity E; Emax refers to the maximum field intensity applied to the oxide layer at a normal operating condition; and τES refers to the estimated value of the oxide layer at a normal operating condition.

Referring to FIG. 2 and FIG. 3, the following description will discuss the steps shown in the flow chart in FIG. 1.

At a step ST11, there are applied, to the oxide layer, electric fields E1, E2, E3, E4 changing according to the field intensity E(t) having a ramp waveform as shown in FIG. 2. At a step ST12, there are measured the electric current densities J1, J2, J3, J4 applied to the oxide layer by applying the electric fields E1, E2, E3, E4, and a time-varying curve J(t) of electric current density is obtained.

At a step ST13, the electric current densities J(t) applied up to the point of time tB when the oxide layer is broken down, are integrated with respect to time t, and the amount Qbd of electric charge used up to the breakdown is calculated. At a step ST14, the electric charge amount Qbd is divided by each of the electric current densities J1, J2, J3, J4 at the measuring points of time t1, t2, t3, t4 on the ramp waveform, thus calculating oxide layer lifetime estimated values τ1, τ2, τ3, τ4 at the field intensities E1, E2, E3, E4. It is known that the total electric charge amount Qbd used up to the breakdown of the oxide layer is a fixed value independent from the field intensity E and the electric current density J. It is therefore understood that each of the oxide layer lifetime estimated values τ1, τ2, τ3, τ4, refers to the period of time between the start of application of each of electric current densities J1, J2, J3, J4 and the breakdown of the oxide layer at the time when it: is supposed that each of the electric current densities J1, J2, J3, J4 was constantly applied to the oxide layer.

At a step ST15, the relationships between the field intensities E1, E2, E3, E4 and the oxide layer lifetime estimated values τ1, τ2, τ3, τ4 are plotted as shown in FIG. 3. From these data, the oxide layer lifetime estimated value τ is approximated in the form of a function of the field intensity E to form a regression line τ(E). At a step ST16, the slope of the regression line τ(E) is extracted as a field acceleration coefficient, and there is determined, using the function of oxide layer lifetime dependent on field intensity, the oxide layer lifetime estimated value τES at the time when the voltage at a normal operating condition is applied to the oxide layer (on the assumption that a fixed maximum field intensity Emax is applied, even though the voltage at a normal operating condition is not always fixed).

According to the basic steps above-mentioned, the stress field acceleration coefficient is extracted and the oxide layer lifetime is estimated.

According to the first embodiment, an electric field increased in the form of a ramp waveform with the passage of time, is applied to the oxide layer, and electric current densities are measured at a plurality of points of time (stress times). Then, the total electric charge amount Qbd is divided by each of the electric current densities to obtain oxide layer lifetime estimated values. Thus, there are obtained, for the same stress times, the field intensities and the lifetime estimated values, based on which a regression line is obtained. More specifically, using the fact that the total electric charge amount Qbd used up to the breakdown of the oxide layer, is a fixed value independent from the field intensity E and the electric current density J, there is obtained each of oxide layer lifetime estimated values on the assumption that each of the electric current densities was applied, as remaining unchanged, to the oxide layer. Based on the lifetime estimated values thus obtained, a regression line is determined. Thus, unlike the conventional lifetime estimation method in which a plurality of constant voltages are applied to a plurality of points of MOS capacitors, the first embodiment is arranged such that a ramp voltage is applied to a single point, and produces the following effects.

First, since stress having a ramp voltage waveform is used, the necessary measurement precision can be assured, yet reducing the measuring period of time to a practically short range. More specifically, even though the total electric charge amount Qbd used up to the breakdown of the insulating layer is extremely small, the electric current density at an early stage of stress application can sufficiently be reduced. It is therefore possible to lengthen the period of time between the start of stress application and the breakdown of the insulating layer, to the extent that the necessary measurement precision can be assured. On the contrary, even though the total electric charge amount Qbd is extremely large, the electric current immediately before the breakdown can sufficiently be increased. This prevents the measuring period of time from being lengthened.

Further, since a field intensity having a ramp waveform is used, it is possible to obtain, through measurement of electric current, voltage and the like of a MOS capacitor, both an insulating layer lifetime estimated value of the MOS capacitor itself at a normal operating condition and a field acceleration coefficient for the MOS capacitor itself. Thus, according to the first embodiment, there is not increased the error in a field acceleration coefficient or insulating layer lifetime estimated value, unlike in the conventional insulating layer lifetime estimation method using different MOS capacitors. That is, the oxide layer lifetime estimation precision is not lowered in spite of reduction in measuring period of time.

Further, a measurement method of embodying an oxide layer lifetime estimation method according to the first embodiment, includes a measurement of the electric current densities at field intensities in a ramp voltage waveform, in addition to a conventional measurement of oxide layer breakdown electric filed distribution and a conventional ramp voltage TDDB measurement. Therefore, the measurement of such electric current densities according to the first embodiment can be made, simultaneously with a conventional oxide layer breakdown electric filed distribution measurement and a conventional ramp voltage TDDB measurement, on each of the same samples used in these conventional measurements. More specifically, the first embodiment is arranged such that with no dedicated sample additionally required, a reliability evaluation of oxide layer on a wafer level can be made simultaneously with measurement of the conventional method with no increase in sample number and measuring period of time. Thus, more information relating to the reliability can be obtained to remarkably enhance the precision of reliability evaluation on oxide layer.

Further, the estimation method of the first embodiment is based on the empirical fact that a total electric charge amount Qbd used up to the breakdown of an insulating layer, is a fixed value independent from field intensity and electric current density. Accordingly, the field acceleration coefficient and the lifetime evaluated value of an oxide layer at a normal operating condition obtained according to the first embodiment, are highly compatible with the field acceleration coefficient and the lifetime evaluated value of an oxide layer at a normal operating condition obtained according to the conventional method.

Accordingly, with the use of the field acceleration coefficient obtained according to the method of the first embodiment, the burn-in condition can suitably be determined in a short period of time.

Test Example Relating to the First Embodiment

The following description will discuss a specific test example of an oxide layer lifetime estimation in a semiconductor device production process, with the use of the method of the first embodiment. In the following, the description will be made of lifetime estimation of an oxide layer serving as a capacitance insulating layer of a MOS capacitor.

In this example, the description will be made of an example of a test for estimating, in a short period of time, the reliability of an oxide layer with the use of a MOS capacitor on a wafer for which the diffusion step has been finished. For each of a number of MOS capacitors having, as capacitor insulating layers, oxide layers to be evaluated, a test was conducted on a wafer level for determining the lifetime estimated value τES according to the following steps. Each of the oxide layers serving as capacitance insulating layers of the MOS capacitors used in this test example, has a thickness of 12 nm, sizes in plane elevation of 100 μm×50 μm, and an area of 5000 μm$^2$. Using a measuring device interlocked with an automatic prober, the points to be measured of the MOS capacitors on a wafer were successively probed to obtain data necessary for lifetime estimation. The measuring device has a voltage source, an electric current source, a voltage meter, an electric current meter and a capacitance meter.

Applied to a MOS capacitor was such a voltage as to bring the MOS capacitor into a charge storage state. For the MOS capacitor formed on a P-type substrate, the voltage of the upper electrode opposite to the voltage of the substrate serving as the lower electrode, was made negative, e.g., set to −5 V. On the contrary, for the MOS capacitor formed on an N-type substrate, the voltage of the upper electrode opposite to the voltage of the substrate, was made positive, e.g., set to +5 V. When the MOS capacitor is in a charge storage state, the capacitance of the oxide layer appears in terms of the capacitance of the MOS capacitor. In this connection, the capacitance of the MOS capacitor was measured, and based on the capacitance thus measured and the oxide layer area, the oxide layer thickness was calculated. The oxide layer thickness is a parameter required for obtaining, from the voltage applied to the oxide layer, the field intensity to be applied thereto.

Applied to the oxide layer was such a voltage as to give an electric field E(t) which undergoes a change in the form of a ramp waveform and which is increased with the time t up to the point of time tB at which the oxide layer is broken down, as shown in FIG. 2. In this example, the ramp voltage increase rate was 0.6 V/sec. At this time, the increase rate of the field intensity E(t) actually applied to the oxide layer was 0.5 MV/cm.sec.

When the voltage source has a function for generating a ramp voltage, this function can be utilized for generating the field intensity E(t) which changes in the form of a ramp waveform. When the voltage source does not have a function for generating a ramp voltage, there can be applied, to the oxide layer, an electric field which simulates a ramp waveform by a step waveform in which each time interval is short within the allowable range in view of time precision of the measuring device, such that the electric field increases proportionally with the passage of time from the start of application of a ramp voltage.

In this test example, the oxide layer was broken down 28 seconds after the start of stress application. In this course, the voltage applied to the oxide layer was divided by the oxide layer thickness obtained earlier, thus obtaining field intensities E1, E2, E3, E4 applied to the oxide layer at the measuring points of time t1, t2, t3, t4. In this example, the measuring points of time t1, t2, t3, t4 are the points of time when the field intensities E1, E2, E3, E4 become 11.5 MV/cm, 12.0 MV/cm, 12.5 MV/cm, 13.0 MV/cm, respectively. Electric currents applied to the oxide layer at the measuring points of time t1, t2, t3, t4 were measured, and the measured values thus obtained were divided by the oxide layer area to obtain the electric current densities J1, J2, J3, J4 at the measuring points of time t1, t2, t3, t4. The electric current densities thus obtained are expressed in the form of a time-varying curve J(t). In this example, the electric current densities J1, J2, J3, J4 on the time-varying curve J(t) are 0.098 A/cm$^2$, 0.18 A/cm$^2$, 0.47 A/cm$^2$, 0.96 A/cm$^2$, respectively.

In this test example, the electric current density J applied to the oxide layer was suddenly greatly increased when the stress application period of time reached 28 seconds. This point of time when the electric current density was suddenly greatly increased, is the point of time tB of the breakdown of the oxide layer. The electric current densities J(t) applied to the oxide layer up to the oxide layer breakdown point of time tB, were integrated with respect to time to calculate the total amount Qbd (C/cm$^2$) of electric charge applied to the oxide layer until the oxide layer was broken down. In this example, the total electric charge amount Qbd was 14 (C/cm$^2$). It is known that the total electric charge amount Qbd is a fixed value independent from the field intensity E and the electric current density J.

Then, the total electric charge amount Qbd was divided by each of the already measured electric current densities 0.098 A/cm$^2$, 0.18 A/cm$^2$, 0.47 A/cm$^2$, 0.96 A/cm at the measuring points of time t1, t2, t3, t4 of the electric field E(t) having a ramp waveform, thus obtaining oxide layer lifetime estimated values τ1, τ2, τ3, τ4 at the field intensities 11.5 MV/cm, 12.0 MV/cm, 12.5 MV/cm, 13.0 MV/cm at the measuring points of time t1, t2, t3, t4. In this test example, the oxide layer lifetime estimated values τ1, τ2, τ3, τ4 were 140 seconds, 78 seconds, 30 seconds, 15 seconds, respectively, at the measuring points of time t1, t2, t3, t4.

The oxide layer lifetime estimated values 140 seconds, 78 seconds, 30 seconds, 15 seconds at the field intensities 11.5 MV/cm, 12.0 MV/cm, 12.5 MV/cm, 13.0 MV/cm, were plotted on a semi-logarithmic graph in which the axis of abscissa represents the field intensity E applied to the oxide layer and the axis of ordinate represents the oxide layer lifetime estimated value τ (logarithm), as shown in FIG. 3. The oxide layer lifetime estimated values 140 seconds, 78 seconds, 30 seconds, 15 seconds at the respective field intensities, were approximated in the form of a function τ(E) of the field intensity E, for example in the form of a regression line. The slope of this regression line was extracted as a field acceleration coefficient β(decades/MV/cm). By utilizing this regression line τ(E), the oxide layer lifetime estimated value at an optional field intensity can be obtained. Thus, using this regression line τ(E), the lifetime estimated value τES of the oxide layer at a normal operating condition is obtained at the maximum field intensity Emax applied to the oxide layer at a normal operating condition.

In this test example, when each of about 50 wafers in one lot for which the diffusion step had been finished, had 5 points to be measured, the whole measurement was finished in a period of time as short as about 1.9 hour during which oxide layer lifetime estimated values were obtained for all the points to be measured of the wafers. According to the first embodiment, measurement for obtaining one oxide layer lifetime estimated value can be made with at least one MOS capacitor, and the measuring period of time per oxide layer can be shortened. Thus, the whole measuring period of time is merely one over several dozens of the measuring period of time taken with the method of prior art. This achieves a remarkable improvement in measurement efficiency.

Figure 10:
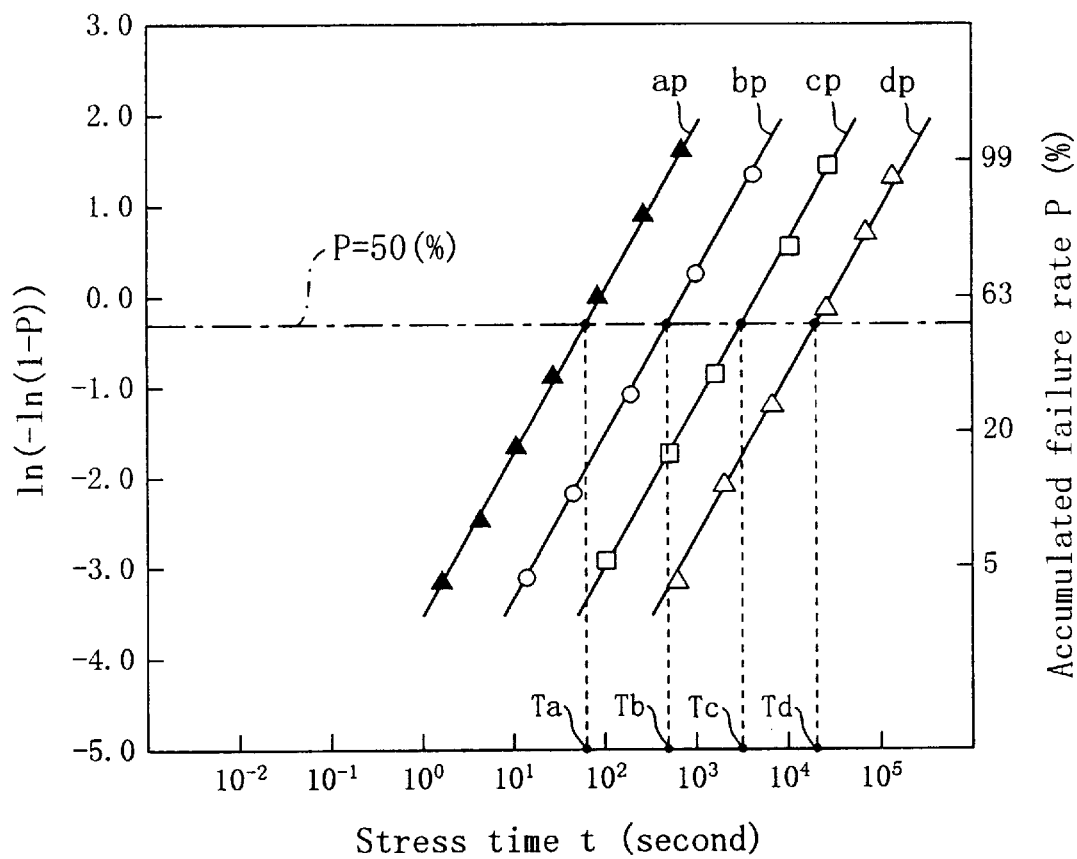
FIG. 10 is a view illustrating the measurement results of oxide layer lifetime at stress field intensities, according to the prior art.
Figure 11:
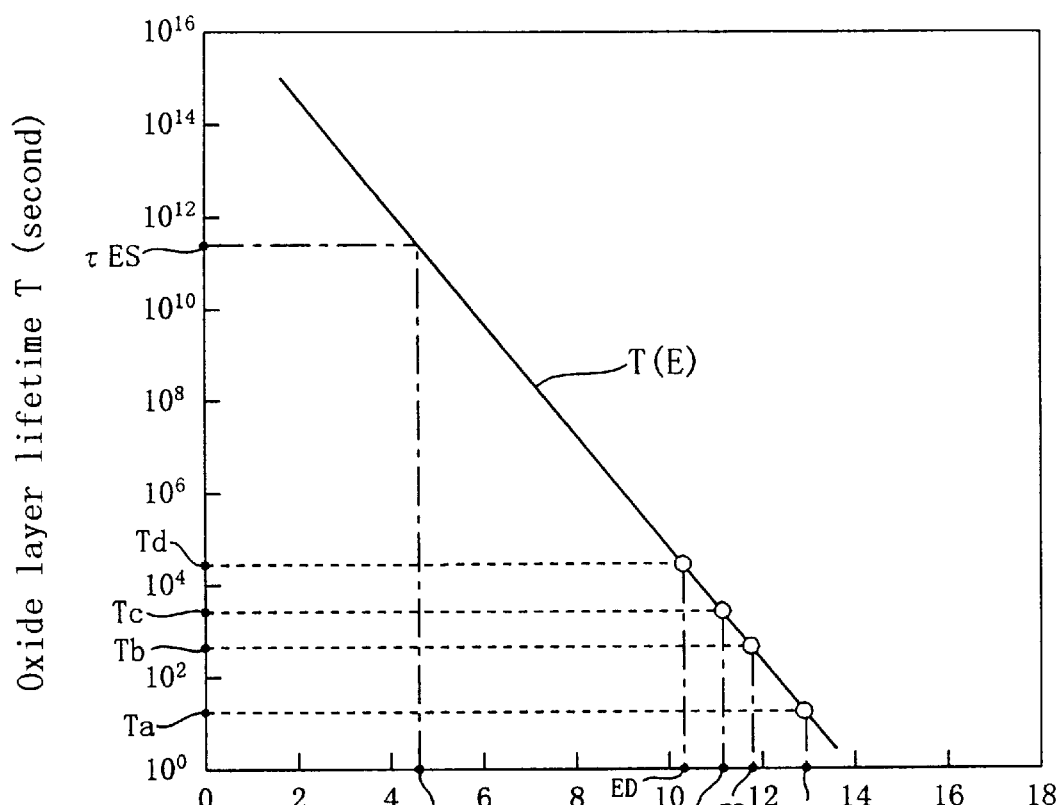
FIG. 11 is a view illustrating a regression line which represents, in the form of a function of the applied voltages, the oxide layer lifetime estimated values obtained according to the prior art, and also illustrating a method of extracting a field acceleration coefficient and estimating an oxide layer lifetime, these extraction and estimation being conducted with the use of this regression line.

In particular, the increase rate of a voltage having a ramp voltage waveform (0.6 V/sec in the above-mentioned example) can be increased such that the period of time between the start of application of the voltage having a ramp voltage waveform and the breakdown of the oxide layer (28 seconds in the above-mentioned example), is shorter than that taken with the use of the smallest stress field intensity out of a plurality of constant stress field intensities in the insulating layer lifetime estimating method of prior art. Further, the increase rate of a voltage having a ramp voltage waveform can be increased such that the maximum intensity of the electric field having a ramp voltage waveform applied to the insulating layer, i.e., the field intensity at which the insulating layer is broken down, is as high as possible unless this disadvantageously introduces the problems that the measuring device becomes poor in time precision and that a high field intensity applied in a test generates heat to cause the period of time up to the time-dependent dielectric breakdown to be shorter than that taken with the use of normal temperature and normal field intensity. By way of example, when the field intensity is made approximately equal to the highest stress field intensity (for example, the field intensity which gives the straight line ap in FIG. 10), out of a plurality of stress field intensities used in the insulating layer lifetime estimating method of prior art, the measuring period of time can be made remarkably shorter than that taken with the lowest stress field (for example, the field which gives the straight line dp in FIG. 10), out of a plurality of stress field intensities used in the insulating layer lifetime estimating method of prior art.

Further, the oxide layer lifetime estimated values at the field intensities in the test example above-mentioned, agree well with the actually measured values. This supports the fact that the field acceleration coefficient and the lifetime estimated value of oxide layer at a normal operating condition according to the first embodiment, are highly compatible with those obtained according to the method of prior art.

(Second Embodiment)

Figure 4:
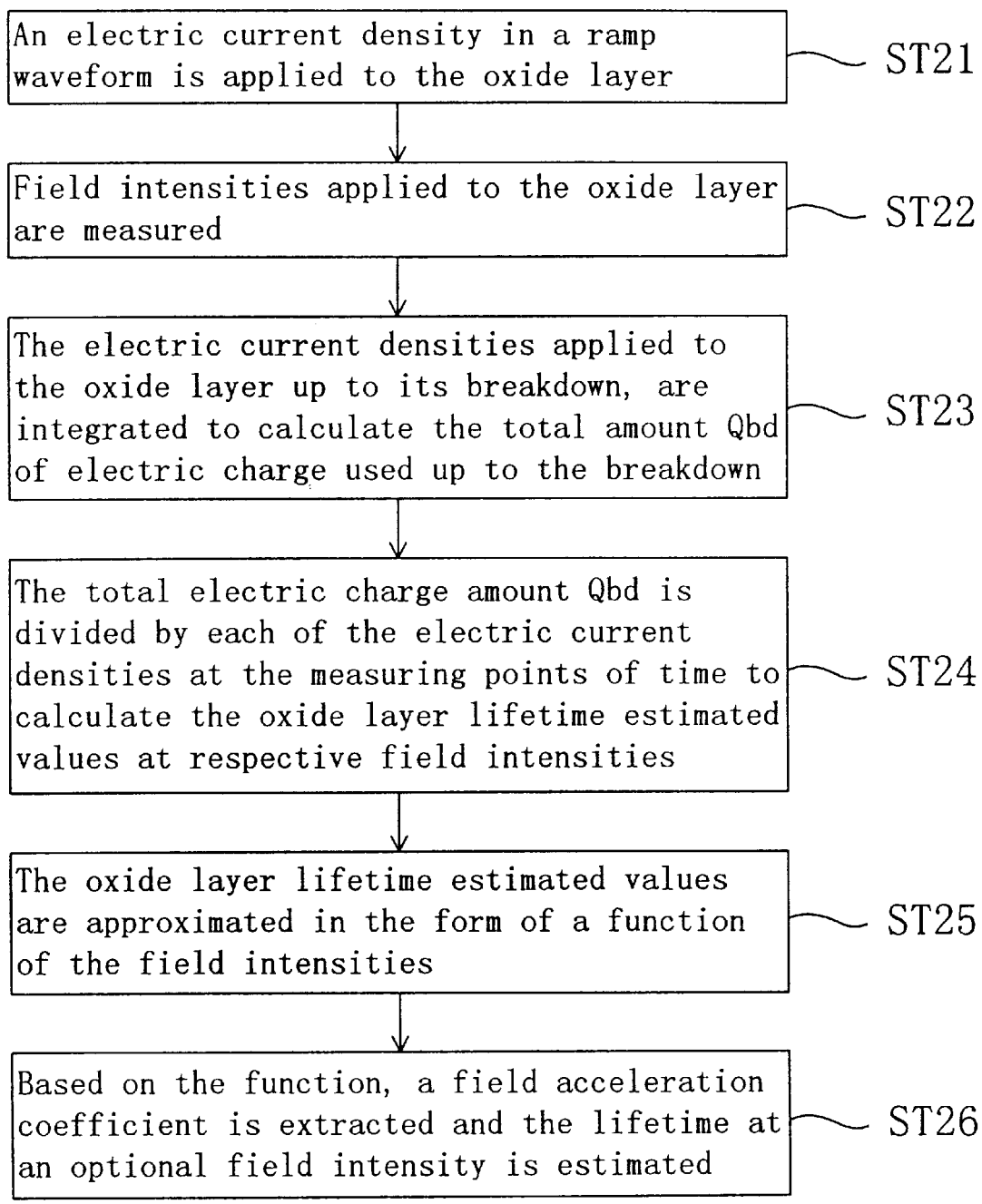
FIG. 4 is a flow chart illustrating the steps of a method of estimating an oxide layer lifetime through a ramp electric current TDDB test, according to a second embodiment of the present invention.
Figure 5:
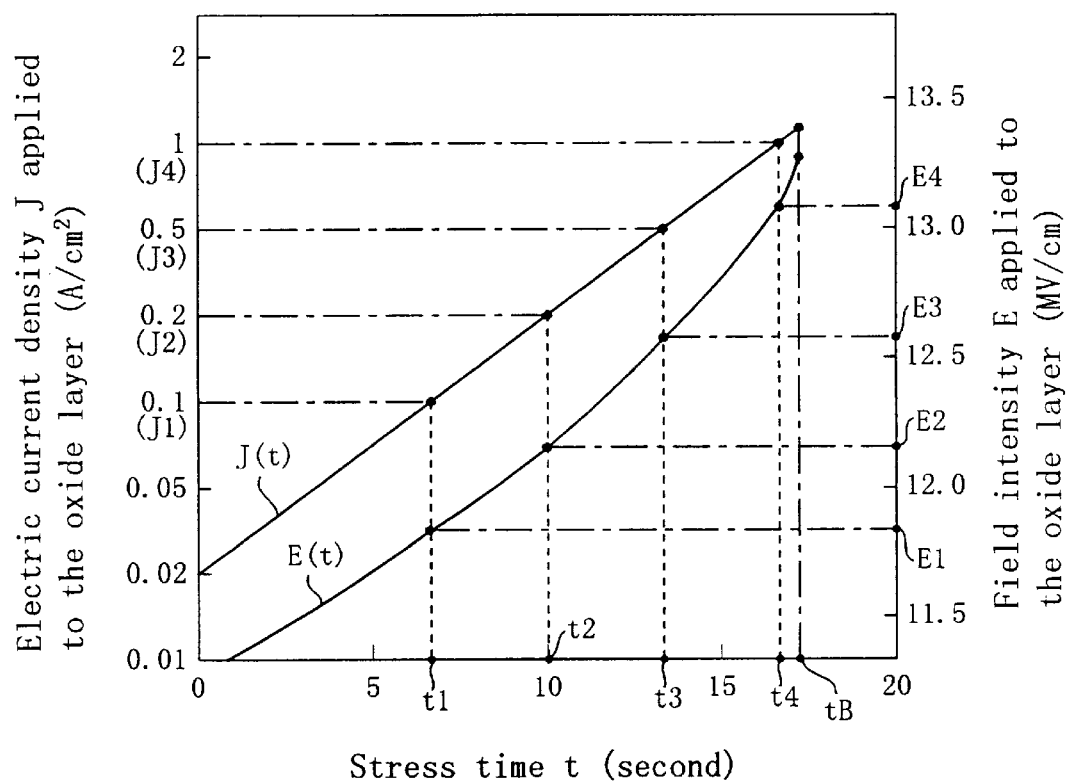
FIG. 5 is a view illustrating the waveform of the ramp electric current and the measurement results of field intensities applied to the oxide layer at the time when the ramp electric current is applied to the oxide layer, according to the second embodiment.
Figure 6:
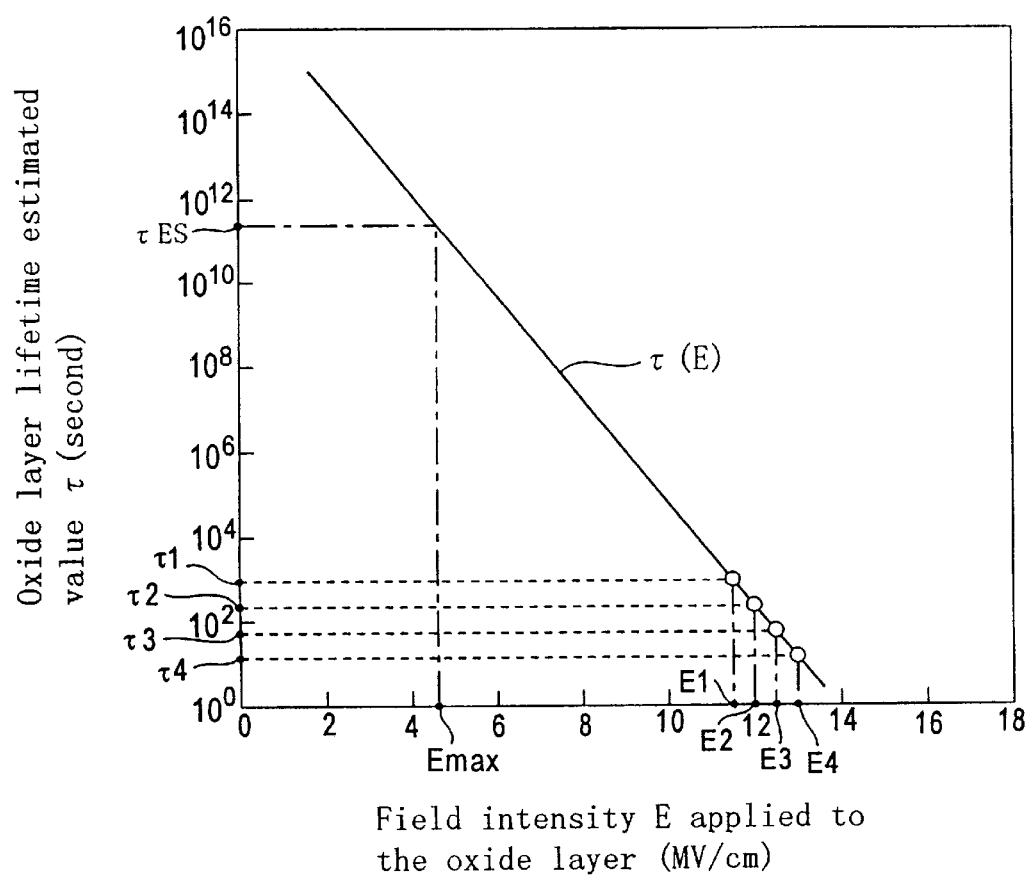
FIG. 6 is a view illustrating a regression line which represents, in the form of a function of the applied voltages, the oxide layer lifetime estimated values obtained according to the second embodiment, and also illustrating a method of extracting a field acceleration coefficient and estimating an oxide layer lifetime, these extraction and estimation being conducted with the use of this regression line.

With reference to FIG. 4 to FIG. 6, the following description will discuss a second embodiment of a method of estimating an oxide layer lifetime through a TDDB test using a ramp electric current. FIG. 4 is a flow chart illustrating the steps of estimating an oxide layer lifetime through a ramp electric current TDDB test. FIG. 5 is a view illustrating the measurement results of field intensities applied to the oxide layer, at the time when an electric current having a ramp waveform (ramp electric current) is applied to the oxide layer until the oxide layer is broken. FIG. 6 is a view illustrating the steps of obtaining a regression line $\tau(E)$ through the ramp electric current TDDB test, and also illustrating the steps of obtaining, with the use of this regression line $\tau(E)$, the oxide layer lifetime estimated value at an optional applied voltage.

In FIG. 5, the axis of abscissa represents stress time t at which an electric current is applied to an oxide layer, the left-hand axis of ordinate represents the electric current density J applied to the oxide layer, and the right-hand axis of ordinate represents the field intensity E applied to the oxide layer. In FIG. 5, J(t) refers to the electric current intensity which is applied to the oxide layer and which changes in the form of a function of time t while describing a ramp waveform; J1, J2, J3, J4 are electric current densities which follow the ramp waveform of the electric current density J(t) and which are applied to the oxide layer at stress application times t1, t2, t3, t4; E(t) refers to the field intensity which is applied to the oxide layer and which is expressed in the form of a function of time; E1, E2, E3, E4 refer to the field intensities which are respectively applied to the oxide layer at the electric current densities J1, J2, J3, J4; and tB refers to stress application time at which the oxide layer is broken down.

In FIG. 6, the axis of abscissa represents the field intensity E applied to the oxide layer and the axis of ordinate represents the oxide layer lifetime estimated value $\tau$. In FIG. 6, $\tau1, \tau2, \tau3, \tau4$ refer to the oxide layer lifetime estimated values at the field intensities E1, E2, E3, E4 applied to the oxide layer; a straight line $\tau(E)$ refers to a lifetime estimation line (regression line) expressed in the form of a function of the field intensity E; Emax refers to the maximum field intensity applied to the oxide layer at a normal operating condition; and $\tau ES$ refers to the estimated value of the oxide layer at a normal operating condition.

Referring to FIGS. 5 and 6, the following description will discuss the steps shown in the flow chart in FIG. 4.

At a step ST21, there are applied, to the oxide layer, electric current densities J1, J2, J3, J4 changing along the electric current density J(t) having a ramp waveform as shown in FIG. 5. At a step ST22, there are measured the electric fields E1, E2, E3, E4 applied to the oxide layer by applying the electric current densities J1, J2, J3, J4, and a time-varying curve of field intensity E(t) is obtained.

At a step ST23, the electric current densities J(t) applied up to the point of time tB when the oxide layer is broken down, are integrated with respect to time t, thus calculating an electric charge amount Qbd used up to the breakdown. At a step ST24, the electric charge amount Qbd is divided by each of the electric current densities J1, J2, J3, J4 at the measuring points of time t1, t2, t3, t4 on the ramp waveform, thus calculating oxide layer lifetime estimated values $\tau1, \tau2, \tau3, \tau4$ at the field intensities E1, E2, E3, E4. It is known that the total electric charge amount Qbd used up to the breakdown is a fixed value independent from the field intensity E and the electric current density J. It is therefore understood that each of the oxide layer lifetime estimated values $\tau1, \tau2, \tau3, \tau4$ refers to the period of time between the start of application of each of the electric current densities J1, J2, J3, J4 and the breakdown of the oxide layer when it is supposed that each of the electric current densities J1, J2, J3, J4 was constantly applied to the oxide layer.

At a step ST25, the relationships between the field intensities E1, E2, E3, E4 and the oxide layer lifetime estimated values $\tau1, \tau2, \tau3, \tau4$ are plotted as shown in FIG. 6. From these data, the oxide layer lifetime estimated value $\tau$ is approximated in the form of a function of the field intensity E to form a regression line $\tau(E)$. At a step ST26, the slope of the regression line $\tau(E)$ is extracted as a field acceleration coefficient, and there is determined, using the function of oxide layer lifetime dependent on field intensity, the oxide layer lifetime estimated value τES at the time when a voltage at a normal operating condition is applied (on the assumption that a fixed maximum field intensity Emax is applied, even though the actual-use voltage is not always fixed).

According to the basic steps above-mentioned, the field acceleration coefficient is extracted and the oxide layer lifetime is estimated.

According to the second embodiment, an electric current density increased in the form of a ramp waveform with the passage of time (ramp electric current), is applied to the oxide layer, and the electric current densities at the measuring points of time (stress times) are measured. The total electric charge amount Qbd is divided by each of the electric current densities at the measuring points of time to obtain oxide layer lifetime estimated values, and the field intensities at the measuring points of time are also measured. Thus, there are obtained, for the same stress times, the field intensities and the lifetime estimated values, based on which a regression line is obtained. More specifically, using the fact that the total electric charge amount Qbd used up to the breakdown of the oxide layer is a fixed value independent from the field intensity E and the electric current density J, there is obtained each of oxide layer lifetime estimated values on the assumption that each of the electric current densities was applied, as remaining unchanged, to the oxide layer. Based on these lifetime estimated values, a regression line is determined. Thus, unlike the conventional lifetime estimation method in which a plurality of constant voltages are applied to a plurality of points of MOS capacitors, the second embodiment is arranged such that a ramp electric current is applied to a single point, and produces the following effects.

First, since an electric current density having a ramp waveform is used, the necessary measurement precision can be assured, yet reducing the measuring period of time to a practically short range. More specifically, even though the total electric charge amount Qbd used up to the breakdown of the insulating layer is extremely small, the electric current density at an early stage of stress application can sufficiently be reduced. It is therefore possible to lengthen the period of time between the start of stress application and the breakdown of the insulating layer, to the extent that the necessary measurement precision can be assured. On the contrary, even though the total electric charge amount Qbd is extremely large, the electric current density immediately before the breakdown can sufficiently be increased. This prevents the measuring period of time from being lengthened.

Further, since an electric current density having a ramp waveform is used, it is possible to obtain, through measurement of electric current, voltage and the like of a MOS capacitor, an estimated value of insulating layer lifetime of the MOS capacitor itself at a normal operating condition and a field acceleration coefficient of the MOS capacitor itself. Thus, according to the second embodiment, there is not increased the error in a field acceleration coefficient or insulating layer lifetime estimated value, unlike in the conventional insulating layer lifetime estimation method using different MOS capacitors. That is, the oxide layer lifetime estimation precision is not lowered in spite of reduction in measuring period of time.

Further, a measurement method of embodying the oxide layer lifetime estimation method according to the second embodiment, includes measurement of field intensities at electric current densities in a ramp voltage waveform, in addition to a conventional ramp electric current TDDB measurement. Accordingly, the measurement of such field intensities according to the second embodiment can be made, simultaneously with a conventional ramp electric current TDDB measurement, on each of the same samples used in the TDDB measurement. More specifically, the second embodiment is arranged such that with no dedicated sample additionally required, a reliability evaluation of oxide layers on a wafer level can be made simultaneously with the conventional method with no increase in sample number and measuring period of time. Thus, more information relating to the reliability can be obtained to remarkably enhance the precision of reliability evaluation on oxide layers.

Further, the estimation method of the second embodiment is based on the empirical fact that the total electric charge amount Qbd used up to the breakdown of an insulating layer, is a fixed value independent from field intensity and electric current density. Accordingly, a field acceleration coefficient and a lifetime evaluated value of an oxide layer at a normal operating condition according to the second embodiment, are highly compatible with those obtained according to a conventional method.

Accordingly, with the use of the field acceleration coefficient obtained according to the method of the second embodiment, the burn-in condition can suitably be determined in a short period of time.

Test Example Relating to the Second Embodiment

The following description will discuss a specific test example of an oxide layer lifetime estimation in a semiconductor device production process, with the use of the method of the second embodiment. In the following, the description will be made of lifetime estimation on an oxide layer serving as a capacitance insulating layer of a MOS capacitor.

In this test example, the description will be made of a method of estimating, in a short period of time, the reliability of an oxide layer using a MOS capacitor on a wafer for which the diffusion step has been finished. For each of a number of MOS capacitors having, as capacitor insulating layers, oxide layers to be evaluated, a test was conducted, on a wafer level, for determining a lifetime estimated value τES according to the following steps. Each of the oxide layers serving as capacitance insulating layers of the MOS capacitors used in this test example, has a thickness of 12 nm, sizes in plane elevation of 100 $\mu$m×50 $\mu$m, and an area of 5000 $\mu$m$^2$. Using a measuring device interlocked with an automatic prober, the points to be measured of the MOS capacitors on a wafer were successively probed to obtain data necessary for lifetime estimation. The measuring device has a voltage source, an electric current source, a voltage meter, an electric current meter and a capacitance meter.

Applied to a MOS capacitor was such a voltage as to bring the MOS capacitor into a charge storage state. For the MOS capacitor formed on a P-type substrate, the voltage of the upper electrode opposite to the voltage of the substrate serving as the lower electrode was made negative, e.g., set to −5 V. On the contrary, for the MOS capacitor formed on an N-type substrate, the voltage of the upper electrode opposite to the voltage of the substrate, was made positive, e.g., set to +5 V. When the MOS capacitor is in a charge storage state, the capacitance of the oxide layer appears in terms of the capacitance of the MOS capacitor. In this connection, the capacitance of the MOS capacitor was measured, and based on the capacitance thus measured and the oxide layer area, the oxide layer thickness was calculated. The oxide layer thickness is a parameter required for obtaining, from the voltage applied to the oxide layer, the field intensity to be applied thereto.

Applied to the oxide layer was such an electric current density J(t) that is increased in the form of a ramp waveform with the time t up to the point of time tB at which the oxide layer is broken down, as shown in FIG. 5. In this test example, the increase rate of the electric current density J(t) in a ramp waveform was 0.1 decade/sec. This means that the electric current density J is increased, with respect to the time t, in an exponential function manner and that the increase rate of the logarithm 1n(J) of the electric current density J with respect to the time t is constant, since "decade" means a digit or a common logarithmic value.

When the electric current source has a function for generating a ramp electric current, this function can be utilized for generating the electric current density J(t) which changes in a ramp waveform. When the electric current source does not have a function for generating a ramp electric current, there can be applied, to the oxide layer, an electric current density which simulates a ramp waveform by a step waveform in which each time interval is short within the allowable range in view of time precision of the measuring device, such that the electric current density has a logarithmic value which proportionally increases with the passage of time from the start of application of a ramp electric current.

In this test example, the oxide layer was broken down 17 seconds after the start of stress application. In this course, the electric current applied to the oxide layer was divided by the oxide layer area, thus obtaining electric current densities J1, J2, J3, J4 at the measuring points of time t1, t2, t3, t4. In this test example, the points t1, t2, t3, t4 on the electric current density curve J(t) in the form of a ramp waveform, are the points of time when the electric current densities J1, J2, J3, J4 become 0.1 A/cm$^2$, 0.2 A/cm$^2$, 0.5 A/cm$^2$, 1.0 A/cm$^2$, respectively. The voltages applied to the oxide layer at the measuring points of time t1, t2, t3, t4 were measured, and the measured values thus obtained were divided by the oxide layer thickness. Thus, there were obtained field intensities E1, E2, E3, E4 applied to the oxide layer at the measuring points of time t1, t2, t3, t4. The field intensities E1, E2, E3, E4 at the four points of time were 11.8 MV/cm, 12.2 MV/cm, 12.7 MV/cm, 13.1 MV/cm, respectively.

In this test example, when the stress application period of time reached 17 seconds, the electric current density J applied to the oxide layer was suddenly greatly increased. The point of time when the electric current density was suddenly greatly increased, is the point of time tB at which the oxide layer was broken down. The electric current densities J(t) applied up to the oxide layer breakdown point of time tB, were integrated to calculate the total electric charge amount Qbd (C/cm$^2$) applied to the oxide layer until the oxide layer was broken down. In this example, the total electric charge amount Qb was 14 (C/cm$^2$).

Then, the total electric charge amount Qbd was divided by each of the already measured electric current densities 0.1 A/cm$^2$, 0.2 A/cm$^2$, 0.5 A/cm$^2$, 1.0 A/cm$^2$ at the points t1, t2, t3, t4 on the ramp waveform curve E(t), thus obtaining oxide layer lifetime estimated values τ1, τ2, τ3, τ4 at the field intensities 11.8 MV/cm, 12.2 MV/cm, 12.7 MV/cm, 13.1 MV/cm at the measuring points of time t1, t2, t3, t4. In this test example, the oxide layer lifetime estimated values τ1, τ2, τ3, τ4 were 140 seconds, 70 seconds, 28 seconds, 14 seconds at the measuring points of time t1, t2, t3, t4.

The oxide layer lifetime estimated values 140 seconds, 70 seconds, 28 seconds, 14 seconds at the field intensities 11.8 MV/cm, 12.2 MV/cm, 12.7 MV/cm, 13.1 MV/cm, are plotted on a semi-logarithmic graph in which the axis of abscissa represents the field intensity E applied to the oxide layer and the axis of ordinate represents the estimated value τ (logarithm), as shown in FIG. 6. The oxide layer lifetime estimated values 140 seconds, 70 seconds, 28 seconds, 14 seconds at the respective field intensities, are approximated in the form of a function τ(E) of the field intensity E, for example in the form of a regression line. The slope of this regression line is extracted as a stress field acceleration coefficient β(decades/MV/cm). By utilizing this regression line τ(E) the oxide layer lifetime estimated value at an optional field intensity can be obtained. Thus, using this regression line τ(B), there can be obtained the lifetime estimated value τES of the oxide layer at a normal operating condition at the maximum field intensity Emax applied to the oxide layer at a normal operating condition.

In this example, when each of about 50 wafers in one lot for which the diffusion step had been finished, had 5 points to be measured, the whole measurement was finished in a period of time as short as about 1.2 hour during which oxide layer lifetime estimated values were obtained for all the points to be measured of the wafers. According to the second embodiment, measurement for obtaining one oxide layer lifetime estimated value can be made with at least one MOS capacitor, and the measuring period of time per oxide layer can be shortened. Thus, the whole measuring period of time is merely one over several dozens of the measuring period of time taken with the method of prior art. This achieves a remarkable improvement in measurement efficiency.

Further, the oxide layer lifetime estimated values at the field intensities in the test example above-mentioned, agree well with the actually measured values. This supports the fact that the field acceleration coefficient and the lifetime estimated value of oxide layer at a normal operating condition according to the second embodiment, are highly compatible with those obtained according to the method of prior art.

(Other Embodiments)

Figure 7:
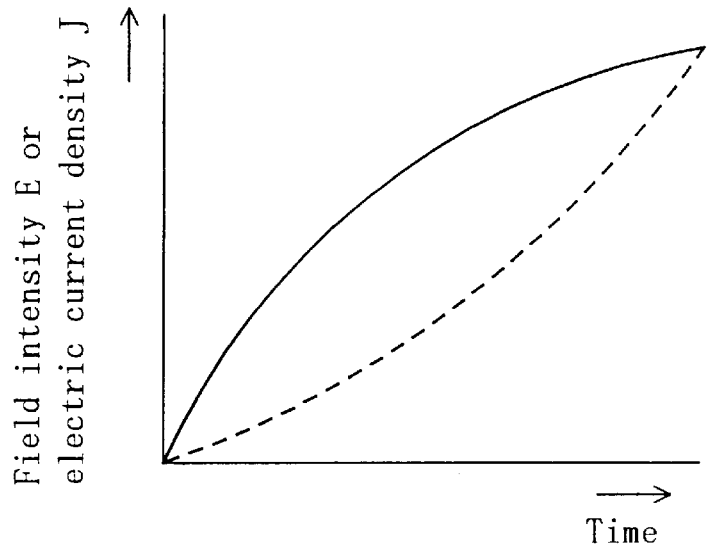
FIG. 7 is a view illustrating an example of field intensity or electric current density which changes in the form of a curve with the passage of time, according to a further embodiment of the present invention.
Figure 8:
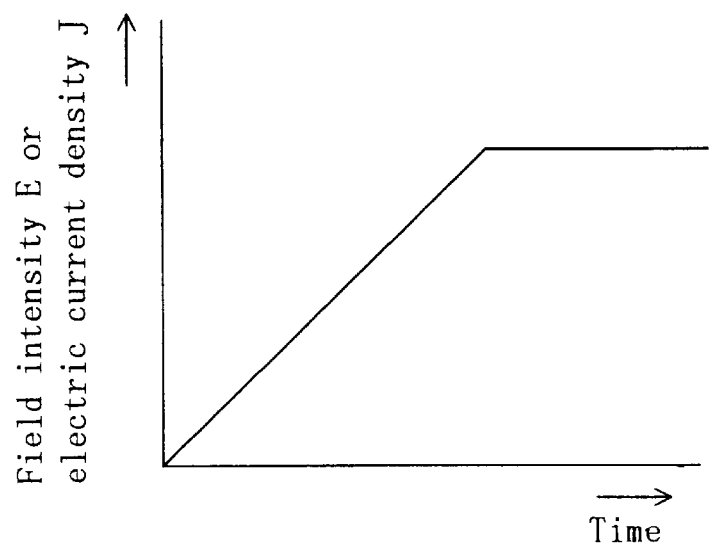
FIG. 8 is a view illustrating an example of field intensity or electric current density which reaches a constant value after having changed in the form of a straight line with the passage of a certain period of time, according to another embodiment of the present invention.
Figure 9:
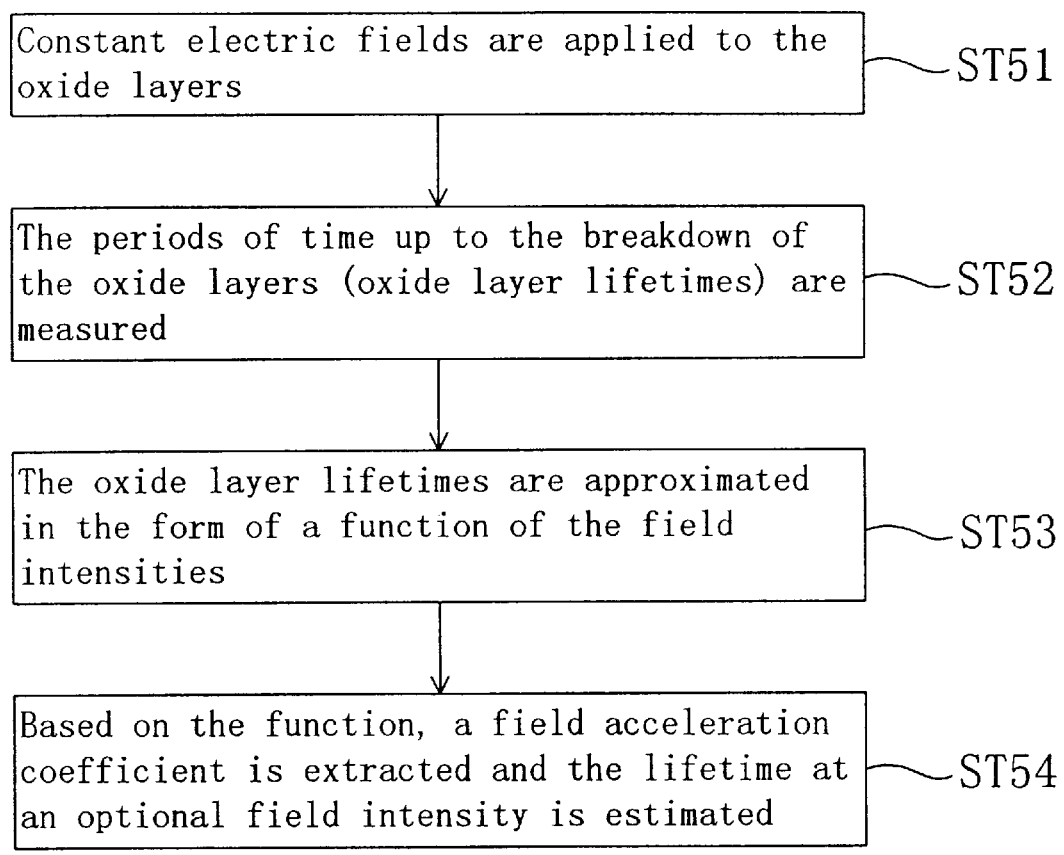
FIG. 9 is a view illustrating the steps of a method of estimating an oxide layer lifetime through a constant voltage TDDB test, according to prior art.

Each of the embodiments above-mentioned is arranged such that there is applied, to the insulating layer, a field intensity or electric current density which is increased at a constant rate. According to the present invention, however, the characteristics of change in field intensity or electric current density to be applied to the insulating layer, are not limited to those in each of the embodiments above-mentioned. For example, there may be applied a field intensity or electric current density having characteristics of change in the form of a curved line as shown by a solid curved line or a broken curved line in FIG. 7. Alternatively, there may be applied a field intensity or electric current density having such characteristics of change that it is linearly increased in a predetermined period of time and then becomes a constant value, as shown in FIG. 8.

In each of FIGS. 2, 5, 7 and 8, the field intensity or electric current density is expressed such that its characteristics of change with the passage of time are continuously increased. However, the field intensity or electric current density is actually mostly expressed such that its characteristics of change with the passage of time are changed in steps.

The steps shown in each of FIG. 1 and FIG. 4 can be stored in a recording medium which can be read by a computer. By incorporating this recording medium in a computer, an insulating layer lifetime estimation can rapidly and automatically be made. As a type of the recording medium, a magnetic disk is commonly used. However, as far as the recording medium can be read by a computer, there may be used any of types of recording medium including a recording medium using other magnetic means (e.g., bubble memory) than a magnetic disk, a recording medium using mechanical concavo-convex patterns such as an optical disk, a recording medium generally called a semiconductor memory such as a ROM utilizing the presence/absence of electric charge or a difference in electric connection, and a recording medium using optical patterns such as a bar coder.

What is claimed is:

1. A semiconductor device evaluation method comprising:

a first step of applying, to an insulating layer disposed in a semiconductor device, an electric field of which intensity undergoes a change with the passage of time;

a second step of measuring the electric current densities applied to said insulating layer at a plurality of points of time during the application of said electric field;

a third step of integrating, with respect to time, said electric current densities applied until said insulating layer is broken down, thereby to calculate the amount of electric charge used until said insulating layer is broken down;

a fourth step of dividing said insulating layer electric charge to breakdown calculated at said third step, by each of said electric current densities at said points of time measured at said second step, thereby to obtain each of the estimated values of insulating layer lifetime at the time when it is supposed that each of said electric current densities at said points of time was constantly applied;

a fifth step of approximating said insulating layer lifetime estimated values in the form of a function of the field intensities; and a sixth step of conducting, based on said function, at least one of an extraction of field acceleration coefficient and an estimation of the insulating layer lifetime at an optional field intensity.

2. A semiconductor device evaluation method according to claim 1, wherein at said sixth step, at least said extraction of field acceleration coefficient is conducted, and using the field acceleration coefficient thus extracted, there is determined the burn-in condition for a product in which said insulating layer is used.

3. A semiconductor device evaluation method according to claim 1, wherein at said first step, there is used an electric field of which intensity between measuring points of time is incremental.

4. A semiconductor device evaluation method according to claim 3, wherein at said first step, there is used an electric field constant in the rate of increase in intensity between measuring points of time.

5. A semiconductor device evaluation method according to claim 3, wherein at said first step, there is used an electric field of which intensity changes in stages with the passage of time.

6. A semiconductor device evaluation method according to claim 1, wherein said first to sixth steps are executed, simultaneously with measurement of breakdown electric filed, on each of the same samples used in said measurement.

7. A semiconductor device evaluation method according to claim 2, wherein a test for the evaluation is conducted, simultaneously with a ramp voltage TDDB test, on each of the same samples used in said TDDB test.

8. A semiconductor device evaluation method comprising:

a first step of applying, to an insulating layer disposed in a semiconductor device, an electric current of which density undergoes a change with the passage of time;

a second step of measuring the electric field intensities applied to said insulating layer at a plurality of points of time during the application of said electric current;

a third step of integrating, with respect to time, said electric current densities applied until said insulating layer is broken down, thereby to calculate the amount of electric charge used until said insulating layer is broken down;

a fourth step of dividing said insulating layer electric charge to breakdown calculated at said third step, by each of said electric current densities at said points of time measured at said second step, thereby to obtain each of the estimated values of insulating layer lifetime at the time when it is supposed that each of said electric current densities at said points of time was constantly applied;

a fifth step of approximating said insulating layer lifetime estimated values in the form of a function of the field intensities; and a sixth step of conducting, based on said function, at least one of an extraction of field acceleration coefficient and an estimation of the insulating layer lifetime at an optional field intensity.

9. A semiconductor device evaluation method according to claim 8, wherein at said sixth step, at least said extraction of field acceleration coefficient is conducted, and using the field acceleration coefficient thus extracted, there is determined the burn-in condition for a product in which said insulating layer is used.

10. A semiconductor device evaluation method according to claim 8, wherein at said first step, there is used an electric current of which density between measuring points of time is incremental.

11. A semiconductor device evaluation method according to claim 10, wherein at said first step, there is used an electric current constant in the logarithmic increase rate of electric current density between measuring points of time.

12. A semiconductor device evaluation method according to claim 10, wherein at said first step, there is used an electric current of which density changes in stages with the passage of time.

13. A semiconductor device evaluation method according to claim 8, wherein a test for the reliability is conducted, simultaneously with a ramp electric current TDDB test, on each of the same samples used in said TDDB test.

* * * * *